United States Patent
Sakai et al.

(10) Patent No.: US 7,695,944 B2
(45) Date of Patent: Apr. 13, 2010

(54) METHOD FOR PRODUCING PHOSHOLIPID

(75) Inventors: Masashi Sakai, Tokyo (JP); Rika Ebina, Tokyo (JP); Hideyuki Yamatoya, Tokyo (JP); Satoshi Kudo, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 351 days.

(21) Appl. No.: 11/654,192

(22) Filed: Jan. 17, 2007

(65) Prior Publication Data
US 2007/0134776 A1   Jun. 14, 2007

Related U.S. Application Data

(63) Continuation of application No. 11/065,974, filed on Feb. 24, 2005, now abandoned, which is a continuation of application No. 10/344,063, filed as application No. PCT/JP01/06502 on Jul. 27, 2001, now abandoned.

(30) Foreign Application Priority Data

Aug. 9, 2000   (JP) ............................. 2000-241034

(51) Int. Cl.
*C12P 5/00*   (2006.01)
(52) U.S. Cl. ...................... 435/166; 435/198; 424/94.1; 424/677
(58) Field of Classification Search .................. 435/166, 435/198; 424/94.1, 677
See application file for complete search history.

(56) References Cited

U.S. PATENT DOCUMENTS

| | | | |
|---|---|---|---|
| 5,733,892 A | 3/1998 | Sakurai et al. | |
| 5,900,409 A | 5/1999 | Sakai et al. | |
| 6,492,146 B1 | 12/2002 | De Ferra et al. | |

FOREIGN PATENT DOCUMENTS

| | | |
|---|---|---|
| EP | 0 288 255 A2 | 10/1988 |
| JP | 63-36792 A | 2/1988 |
| JP | 63-263089 A | 10/1988 |
| JP | 3-291289 A | 12/1991 |
| JP | 7-16426 B2 | 3/1995 |
| JP | 2942302 B2 | 6/1999 |

OTHER PUBLICATIONS

S.F. Yang et al., "Transphosphatidylation by Phospholipase D", *The Journal of Biological Chemistry*, vol. 242, No. 3, pp. 477-484.
Y. Kokusho et al., "Purification and Properties of Phospholipase D from Actinomadura sp. Strain No. 362", *Agric. Biol. Chem.*, vol. 51 (9), pp. 2515-2524 (1987).

*Primary Examiner*—Ruth A Davis
(74) *Attorney, Agent, or Firm*—Frishauf, Holtz, Goodman & Chick, P.C.

(57) ABSTRACT

A method for producing a phospholipid using transphosphatidylation, which comprises homogenizing a mixture of a raw material phospholipid, a hydroxyl-containing acceptor, phospholipase D, and water in the absence of an organic solvent to obtain a homogenized mixture; and subjecting the homogenized mixture to a transphosphatidylation reaction at 15° C. to 65° C. The homogenized mixture has a lamellar lyotropic liquid crystal structure. An objective phospholipid can be obtained from the homogenized mixture through transphosphatidylation without using an organic solvent or calcium.

10 Claims, 4 Drawing Sheets

METHOD FOR PRODUCING PHOSHOLIPID

CROSS-REFERENCE TO RELATED APPLICATIONS

This application is a continuation application of application Ser. No. 11/065,974 filed Feb. 24, 2005 now abandoned, which is a continuation application of application Ser. No. 10/344,063 filed Feb. 6, 2003 now abandoned, which is a United States national phase application of PCT/JP01/06502 filed Jul. 27, 2001, the entire contents of said applications being incorporated by reference herein.

TECHNICAL FIELD

The present invention relates to a method for producing an objective phospholipid using transphosphatidylation (phospholipid base exchange reactions).

BACKGROUND ART

Phospholipids such as phosphatidylserines (PSs) and phosphatidylglycerols (PGs) each have their useful physiological or biological functions and specific physical properties and are used in, for example, pharmaceutical preparations, food materials, and emulsifying agents. For example, phosphatidylserines are promising as drugs for prophylaxis and/or therapy of senile dementia and dysmnesia (memory disorder), phosphatidylglycerols are promising as emulsifying agents, and phosphatidylascorbic acids are promising as emulsifying agents and lipoperoxides inhibitors.

These phospholipids have been conventionally produced by chemical synthesis or by transphosphatidylation using phospholipase D. Among these production methods, enzymatic methods can relatively easily produce phospholipids at relatively low cost and are widely used.

Methods for producing objective phospholipids by transphosphatidylation (phospholipid base exchange reactions) have been known from a long time ago (Yang, S. F. et al., J. Biol. Chem., 242, p. 477, 1967). For example, Kokusho et al. disclose that a reaction product containing phosphatidylserine is obtained by a biphasic reaction in which phospholipase D is allowed to act upon a mixture of a solution of egg-yolk phosphatidylcholine in isopropyl ether with a L-serine aqueous solution containing calcium chloride (Agric. Biol. Chem., 51, p. 2515, 1987). It is generally believed that a reaction system in such a biphasic reaction comprises two phases of an oil phase containing a material phospholipid and an aqueous phase containing an acceptor and that transphosphatidylation occurs at the interface between the two phases.

Japanese Patent No. 2,942,302 describes a homogenous reaction in which a phospholipid preparation containing about 85% of phosphatidylcholine prepared by fractionating soybean lecithin is dissolved in ethyl acetate, the resulting solution is mixed with an ascorbic acid aqueous solution to yield a mixture, and the mixture is allowed to react with phospholipase D to thereby yield a reaction product containing phosphatidyl ascorbate.

However, the biphasic reaction must be carried out in the presence of solvents (an organic solvent and water) five times or more (volume/weight) as much as the phospholipid and thereby must use a reactor having a volume capacity six times as much as the amount of the phospholipid. In addition, calcium added to accelerate the reaction rapidly forms a salt with the phospholipid. The formed calcium salt is belonging to the category of chemically synthesized substances in Japan and Europe, and the product is thereby difficult to use in food.

In the homogenous reaction (monophasic reaction), the reaction system contains large amounts of water and yields a phosphatidic acid, as a by-product, due to hydrolytic activity of phospholipase D during a continuous reaction, thus the separation and purification of the objective phospholipid becoming difficult. In addition, the proportion of the acceptor to the phospholipids is limited in the homogenous reaction, and thereby the production amount of the objective reaction product (phospholipid) is limited.

A patent granted to Fujita et al. (JP-B-7-016426) describes that phosphatidylserine, phosphatidylglycerol, and others are produced by a reverse micelle reaction in which an aqueous phase containing calcium chloride, a hydroxyl-containing acceptor, and phospholipase D and being encapsulated in a reversed micelle is allowed to react with a solution of a raw material phospholipid in an organic solvent (diisopropyl ether, isooctane, cyclohexane, benzene, chloroform-isooctane, n-hexane, or dichloromethane-isooctane).

In the Japanese Patent Publication, Fujita et al. report that the reverse micelle reaction requires only a small amount of water and thereby suppresses the formation of phosphatidic acids, the problem of the above method. However, the method in question insufficiently yields the objective phospholipid in a yield of at most about 20%, requires complicated operations such as ultrasonic treatment and thus invites problems in operability and cost. The method also requires the organic solvent 10 times (volume/weight) as much as the phospholipid and must use a reactor having a capacity many times as much as the amount of the phospholipid.

These conventional transphosphatidylation reactions must be carried out in a reaction system containing an organic solvent. However, when product phospholipids are used in, for example, food and pharmaceutical preparations, the organic solvent must not remain in the products and must be completely removed. Accordingly, their production process steps require facilities for the removal of the organic solvent, thus inviting disadvantages in; for example, operability and cost. In particular, such organic solvents cannot be substantially used in the reactions based on the food sanitation law when the products are used in the production of food.

Demands have therefore been made on methods for producing phospholipids without using organic solvents and/or calcium salts. However, one skilled in the art generally believes that a reaction does not smoothly proceed without using organic solvents and thereby the yield of the objective phospholipid and operability should decrease, since the material phospholipids such as phosphatidylcholines are oil-soluble.

DISCLOSURE OF INVENTION

Accordingly, an object of the present invention is to provide a method for producing phospholipid by transphosphatidylation, using phospholipase D, which can easily produce the objective phospholipid in a high yield without using organic solvents and/or calcium.

Thus, according to the present invention, the above object can be achieved by a method for producing phospholipid through transphosphatidylation, comprising the steps of homogenizing a mixture of a raw material phospholipid, a hydroxyl-containing acceptor (accepter having one or more hydroxyl groups), phospholipase D, and water in the absence of an organic solvent to obtain a homogenized mixture; and subjecting the homogenized mixture to a transphosphatidylation reaction at a temperature within a range from 15° C. to 65° C.

In the method according to the present invention, the four components, the raw material phospholipid, the hydroxyl-containing acceptor, phospholipase D, and water, are sufficiently mixed, and the resulting mixture is further homogenized. The homogenized mixture is supposed to have a lamellar lyotropic liquid crystal structure. The term "lamellar lyotropic liquid crystal" means a liquid crystal of a phospholipid bilayer membrane formed by adding water to a phospholipid. In the present invention, it is supposed that the homogenized mixture has an array structure containing the bilayer membrane (sometime a polymolecular layer membrane structure) and an aqueous layer alternately continuously arrayed. The lamellar lyotropic liquid crystal structure can be identified by, for example, microscopic observation of the homogenized mixture under crossed Nicols.

In this connection, a "lamellar lyotropic liquid crystal structure substantially without phase separation" mentioned later and a "lamellar lyotropic liquid crystal structure with phase separation" are observed as a continuous lamellar structure and as a closed-ring structure floated in an aqueous phase, respectively.

The lamellar lyotropic liquid crystal structure is generated in the following manner. That is, by adding water to the raw material phospholipid in the homogenization procedure, the interaction between hydrophilic groups in the phospholipid becomes weak, and its crystal structure disintegrates to forme a lamellar liquid crystal. Because of the formation of the lamellar lyotropic liquid crystal structure, water can freely move between layers of the lamellar structure of the phospholipid to make it efficient to supply the acceptor and/or the enzyme and to remove polar heads liberated from the phospholipid, thereby enabling a transphosphatidylation reaction.

To increase the yield of the reaction product, the entire homogenized mixture must have the lamellar lyotropic liquid crystal structure. For that purpose, the individual components must be homogenized in addition to simply mixed. In other words, the entire homogenized mixture preferably has the lamellar lyotropic liquid crystal structure (i.e., the mixture substantially has the lamellar lyotropic liquid crystal structure) as a result of homogenization for a higher yield of the reaction product.

A water content in the homogenized mixture affects the formation of the lamellar lyotropic liquid crystal structure. If the water content is within a specific range (e.g., from about 10 wt % to about 100 wt % relative to the amount of soybean phospholipid), the homogenized mixture will have a lamellar (neat) liquid crystal with substantially no phase separation. However, if the water content is excessively higher than the specific range, the homogenized mixture may undergo phase separation to form two phases containing a liquid and a liquid crystal. In the method according to the present invention, the reaction is preferably performed while the homogenized mixture is without phase separation or with substantially no phase separation (hereinafter both are referred to as "lamellar lyotropic liquid crystal structure substantially without phase separation") for a further higher transfer activity.

In contrast, in a homogenized mixture containing an excessively large amount of water to thereby invite phase separation (a lamellar lyotropic liquid crystal structure with phase separation), the liquid crystal may constitute discontinuous small granules floating in the solvent. Accordingly, the contact efficiency between water and the phospholipid decreases, thus decreasing transfer activity as compared with the case without phase separation. If the water content is excessively low, the phospholipid may maintain its crystal structure to inhibit the formation of a lamellar lyotropic liquid crystal structure overall the phospholipid to thereby lose the field of an enzymatic reaction. Alternatively, the homogenized mixture may have decreased fluidity and thereby have a deteriorated contact efficiency between the substrate and the enzyme, thus the enzyme cannot efficiently act upon the substrate.

Organic solvents are preferably not used in the homogenization procedure. If an organic solvent is added during the homogenization procedure, phase separation as in conventional biphasic reactions (not phase separation in the lamellar lyotropic liquid crystal structure but separation between an oil phase and an aqueous phase) may be enhanced. In addition, the addition of an organic solvent invites various disadvantages as described above.

Raw material phospholipids for use in the present invention include any of phospholipid-containing natural products, extracts or purified extracts of such natural products, and synthetic phospholipids. Examples of the phospholipids include, but are not limited to, soybean lecithin, rapeseed lecithin, egg yolk lecithin, corn lecithin, cottonseed lecithin, purified products of these lecithins; phosphatidylcholines (hereinafter briefly referred to "PC(s)"), phosphatidylethanolamines (hereinafter briefly referred to as "PE(s)"), and mixtures of these substances. Among them, soybean lecithin, rapeseed lecithin, egg yolk lecithin, and purified products of these lecithins are preferred for their availability and cost.

Hydroxyl-containing acceptors for use in the present invention are not specifically limited as long as they can receive or accept a phosphatidyl group of the raw material phospholipid in the presence of phospholipase D. Such hydroxyl-containing acceptors include, for example, serine, glycerol, L-ascorbic acid, glucose, choline, ethanolamine, 1-amino-2-propanol, and 1-o-methyl-glycoside. Among them, serine, choline, L-ascorbic acid, glucose, and glycerol are preferred for a higher yield of the objective product, of which serine and glycerol are typically preferred.

Phospholipase Ds (hereinafter briefly referred to as "PLD(s)") for use herein are not specifically limited as long as they have transphosphatidylation activity and include, for example, free or chemically modified PLDs, and immobilized enzymes immobilized to a carrier such as ion exchange resins and silica gel. Among them, free PLDs are preferred for a further higher yield of the reaction product.

More specifically, any of PLDs derived from plants or vegetables such as cabbage and carrot, PLDs derived from microorganisms such as mycobacteria, bacteria, yeasts, and fungi (molds), and PLDs derived from animals can be advantageously used. They may be prepared products prepared according to a conventional procedure or commercially available products such as a cabbage-derived PLD (e.g., Product Number P 7758, Sigma Chemical Company), peanut-derived PLD (e.g., Product Number P 0515, Sigma Chemical Company), and a PLD derived from *Streptomyces chromofuscus*.

According to the present invention, the raw material phospholipid, the hydroxyl-containing acceptor, PLD, and water are initially mixed, and the resulting mixture is further subjected to a homogenization procedure. The homogenization procedure herein means homogenous dispersion of the four components in the mixture by the application of physical force by means of, for example, physical agitation, ultrasonic treatment, etc. More specifically, homogenization treatments using a Vibromixer, automatic mortar, Homo Mixer, Physcotron, food processor, or sonicator alone or in combination can be employed. If the amount of the mixture is small, it may be kneaded using, for example, a microspatula. The four components may be mixed and homogenized separately in time or simultaneously. For example, one of the four components may be mixed and homogenized with another, and this procedure is repeated. It is also acceptable that two, three or four of the components are mixed or dissolved in advance, and then the resulting mixture or solution is ultimately homogenized.

If the homogenization procedure is not performed in the method of the present invention, the yield of the objective phospholipid significantly decreases. This is probably for the following reasons. That is, the raw material phospholipid is generally a hard paste at room temperature, and the entire mixture cannot have a lamellar lyotropic liquid crystal structure by simply mixing the other components. As a result, the individual components come in contact with one another at a lower frequency to thereby decrease the yield of the objective product. Accordingly, the mixture of the components must be applied with physical force to such an extent as to disperse the individual components and must be subjected to a "homogenization procedure".

The hydroxyl-containing acceptor can be used as an aqueous solution or as a powder in the homogenization procedure. PLD is used as a solution in a small amount of water or as a powder. In this procedure, if the other three (the raw material phospholipid, PLD, and water) than the acceptor have been mixed in advance, phosphatidic acid (hereinafter referred to as "PA") is byproduced. Accordingly, it is preferred that the raw material phospholipid is mixed with the acceptor in advance, and the resulting mixture is then mixed with the other components, or the four components are mixed and homogenized simultaneously.

As is described above, the amount of water content in the homogenization procedure affects the phase separation of the lamellar lyotropic liquid crystal structure and the yield of the reaction product phospholipid and is preferably controlled and adjusted to prevent the phase separation. While depending on the type of the raw material phospholipid, the water content in the lamellar lyotropic liquid crystal structure is preferably from 10 wt % to 100 wt % and more preferably from 20 wt % to 60 wt % relative to the amount of the raw material phospholipid to substantially prevent the phase separation. The term "water content" in the lamellar lyotropic liquid crystal structure as used herein means the amount of water in the homogenized mixture after removing water separated during the homogenization procedure and can be determined by, for example, a conventional Karl Fischer technique. The separated water may be removed by decantation or centrifugal separation, for example, at 150 g for about 1 minute.

It is not necessarily appropriate to specify a preferred amount of the acceptor, since it varies depending on the type of the acceptor. For a better yield of the reaction product and operability, the amount is preferably from about 0.3 mole to about 10 moles and more preferably from about 4 moles to about 8 moles per 1 mole of the raw material phospholipid. If an excessively large amount (exceeding 10 moles) of the acceptor is added, the recovery of an unreacted acceptor may require increased efforts. In contrast, if the amount is excessively small, the yield of the objective product may decrease.

More specifically, the amount of serine as the hydroxyl-containing acceptor is preferably from 5 wt % to 150 wt %, and more preferably from 50 wt % to 100 wt % relative to the amount of the raw material phospholipid. The amount of glycerol as the hydroxyl-containing acceptor is preferably from 10 wt % to 200 wt %, and more preferably from 20 wt % to 100 wt %.

The amount of PLD is not specifically limited, can be determined depending on, for example, the reaction time in the subsequent reaction step and is generally from about 500 to 100,000 units per kg of the phospholipid.

A temperature in the homogenization procedure is not specifically limited and is preferably from about 15° C. to 65° C. If the temperature is lower than 15° C., it may require extra energy to cool the reaction system, and the mixture may not sufficiently be homogenized. If it is higher than 65° C., the phospholipid may become unstable.

In addition to the aforementioned components, an edible oil and/or fat can be added during the homogenization procedure within ranges not deteriorating the lamellar lyotropic liquid crystal structure. Although the addition of such an edible oil and/or fat enhances the conversion of the lamellar lyotropic liquid crystal structure into a biphasic system as organic solvents, a small amount of the edible oil and/or fat increases the fluidity of the homogenized mixture to thereby increase the yield of the objective phospholipid. Such edible oils and fats include, but are not limited to, safflower oil, soybean oil, corn oil, rapeseed oil, cottonseed oil, sunflower oil, safflower oil, sesame oil, olive oil, hempseed oil, perilla oil, theobroma oil (cacao butter), coconut oil, and other vegetable oils; butter oil, fish oil, lard, beef tallow, and other animal oils; and middle-chain triacylglycerols (MCTs). Each of these oils and fats is added alone or in combination to the raw material phospholipid to impart fluidity thereof. Among them, MCTs, theobroma oil, and soybean oil are preferred to further improve the yield of the objective product.

While depending on the types of the raw material phospholipid and the added edible oil and/or fat, the amount of the edible oil and/or fat is preferably less than or equal to an equivalent amount and more preferably from 5 wt % to 15 wt % relative to the amount of the raw material phospholipid.

It is possible to add an organic solvent such as hexane or ether for the same purpose within ranges not deteriorating the lamellar lyotropic liquid crystal structure, but is not preferred as described above.

Some of advantages of the present invention will be described hereinafter Conventional transphosphatidylation reactions have been performed according to any of biphasic reactions, reversed micelle reactions, and homogenous phase reactions. The biphasic reactions and reversed micelle reactions require a solvent five times (volume/weight) or more as much as the phospholipid to maintain their reaction systems. In contrast, the method of the present invention requires a solvent only one time as much as the phospholipid and can thereby use a reactor having a smaller capacity for the production of the phospholipid in the same amount as in the conventional equivalents.

The homogenous phase reactions require a solvent two times (volume/weight) or more as much as the phospholipid and thereby require a reactor having a capacity three times (volume/weight) or more as much as the phospholipid. In addition, the amount of the acceptor is limited to maintain their homogenous phase, and it is difficult to obtained a reaction product containing the objective compound in a high content. For example, to produce PS, the amount of serine that can be added to 1 kg of the phospholipid is 0.15 kg and the PS content in the reaction products phospholipids is at most 35%. In contrast, according to the method of the present invention, 1 kg or more of serine can be added to 1 kg of the phospholipid, and thereby reaction products containing 48% or more of PS in the phospholipids can be obtained. Specifically, the method of the present invention can reduce the capacity of a reactor to produce an equivalent amount of the objective phospholipid and can yield reaction products containing the objective compound in a high content as compared with the homogenous reactions.

Each of the conventional transphosphatidylation reactions must be performed in the presence of an organic solvent such as an ether, toluene, n-hexane, or ethyl acetate in their reaction system. However, the method according to the present invention does not require organic solvents and is therefore advantageous in the production of the phospholipids for food and other substances in which the use of organic solvents is restricted. Further, according to the present invention, the reaction proceeds even without the addition of calcium ions in contrast to the conventional methods. While not being clarified, this is probably because the reaction is performed in a liquid crystal according to the present invention and thereby the raw material phospholipid becomes structurally susceptible to transphosphatidylation reactions regardless of the presence or absence of calcium ion. In contrast, the conventional biphasic reaction is performed in a liquid.

According to the present invention, the homogenized mixture thus obtained is subjected to a transphosphatidylation reaction in the absence of an organic solvent to yield the objective phospholipid. The reaction is performed at a temperature preferably within a range from 15° C. to 65° C. and more preferably from 45° C. to 55° C. If the reaction temperature is lower than 15° C., the reaction may not be enhanced to proceed to thereby deteriorate the yield of the objective phospholipid. If the reaction temperature is higher than 65° C., side reactions of phospholipid, such as decomposition and/or oxidation of the produced phosphatidylserine, may occur.

A reaction time is not specifically limited, can be appropriately selected depending on the reaction temperature, the types and amounts of the components and is preferably from about 1 to 48 hours for a better yield of the objective phospholipid and less by-production of PA.

The transphosphatidylation reaction can be performed left stand or with stirring. For example, the reaction can be performed with stirring using a tabletop universal mixer (e.g., KINMIX MAJOR (trademark), Type-KM-230).

In the production of phospholipids according to the method of the present invention, a lamellar liquid crystal structure without phase separation is formed entirely in the homogenized mixture by mixing an appropriate amount of water with the raw material phospholipid, and water can freely move between layers of the lamellar structure of the phospholipid, thereby efficiently supplying the hydroxyl-containing acceptor and/or the enzyme as well as efficiently removing polar heads liberated from the phospholipid. Accordingly, it is possible to achieve the transphosphatidylation reaction at high activity, and the objective phospholipid can be easily obtained in high yield at low cost.

Phospholipids obtained according to the present invention may contain impurities derived from the raw material phospholipid and the acceptor, and other substances in addition to by-product PA. The obtained phospholipid is therefore often a phospholipid mixture containing the objective phospholipid, other phospholipids and impurities.

The phospholipid obtained by the transphosphatidylation is preferably used after the removal of such impurities by subjecting the same to an appropriate purification process but can be used while containing impurities derived from the raw materials or formed in the production processes as long as the impurities do not invite problems in administration or deteriorate the advantages. The product can be purified by any technique such as fractionation using a solvent and chromatography in appropriate combination according to a conventional procedure.

The phospholipids obtained according to the present invention can be administered in the form of, for example, pharmaceutical preparations, food, or cosmetics. For example, to be used in the form of pharmaceutical preparations to utilize the biological functions of the phospholipids, they can be orally administered in the dosage form of, for example, capsules, granules, tablets, powders, and other solid preparations; and syrups, and other liquid preparations. Alternatively, they can be administered in the form of, for example, injections, dermatologic external preparations, rectal infusions, and other non-oral preparations.

In production of these preparations, additional pharmaceutically acceptable components can be used according to necessity. Such components include, for example, lactose, starches, crystalline cellulose, calcium lactate, magnesium aluminometasilicate, silicic anhydride, and other excipients; sucrose, hydroxypropylcellulose, polyvinylpyrrolidone, and other binders; carboxymethylcellulose, carboxymethylcellulose calcium, and other disintegrators; magnesium stearate, talc, and other lubricants.

When the phospholipid obtained according to the method of the present invention is used in food in the expectation of similar biological functions, such food can be appropriately produced according to a conventional procedure by adding the phospholipid as intact or after purification to oils and fats, tablet or granular confectionery, fermented milk candies, spices, fish and vegetables flakes to sprinkle on cooked rice, and other food and drinks.

An appropriate amount of the phospholipids obtained by the method of the present invention can be used in the form of these pharmaceutical preparations and food. To obtain the biological functions of the phospholipids, the amount thereof may be such as to yield the functions and not to invite problems such as overdose. For example, the compositional amount of phosphatidylserine produced as the phospholipid is such an amount as to take in from about 50 mg to 1,000 mg a day.

The phospholipids obtained by the method according to the present invention can also be used as emulsifying agents. In this case, the emulsifying agent may be added to, for example, pharmaceutical preparations, food, and cosmetics in an amount preferably from 0.01% to 10%.

Among phospholipids obtained by the method according to the present invention, a phosphatidylserine can be easily purified and concentrated from a phospholipid mixture containing the phosphatidylserines by dissolving the phospholipid mixture in an alcohol to yield a solution, adding a metallic salt to the solution to insolubilize the phosphatidylserines, and separating the insolubilized matter.

Such metallic salts for use herein include, but are not limited to, lithium salts, sodium salts, potassium salts, calcium salts, magnesium salts, and other metallic salts, as well as natural products containing any of these metallic salts in abundance, such as common salt, bittern, brine, dolomite, and edible powdery mother of pearl. Among them, lithium salts, sodium salts, and potassium salts are preferred for efficient concentration, of which lithium chloride, sodium chloride, and potassium chloride are typically preferred. Each of these metallic salts can be used alone or in combination.

The amount of the metallic salt(s) is not specifically limited as long as phosphatidylserine can be precipitated and is preferably from 0.15 to 10 mmol, and more preferably from 0.5 to 5 mmol per gram of the phospholipid for a higher recovery rate of the phosphatidylserines and a higher content of the phosphatidylserines in the precipitate.

Any alcohol can be used herein as long as it can dissolve the phospholipid mixture, of which methyl alcohol, ethyl alcohol, butyl alcohol, propyl alcohol, isopropyl alcohol, and other lower alcohols are preferred. Mixtures of these alcohols can also be used. Ethyl alcohol can be easily applied to food with less problems in safety and is typically advantageously used.

The concentration of the phospholipid mixture in the alcohol is not specifically limited, is preferably equal to or more than such a concentration that the mixture can be completely dissolved in the alcohol and is preferably from 1 to 50%, and more preferably from 2 to 20% relative to the weight of the alcohol for efficient concentration procedure of the phosphatidylserines and for higher operability.

The phosphatidylserines can be concentrated from the phospholipid mixture, for example, in the following manner. Initially, the phospholipid mixture prepared by transphosphatidylation and containing other phospholipids in addition to the phosphatidylserines is dissolved in an alcohol such as ethyl alcohol. In this procedure, dissolution conditions such as dissolution temperature are not specifically limited and can be appropriately selected depending on the types and amounts of components of the mixture and other parameters.

In the resulting solution, the phosphatidylserines, PC, PA, and other phospholipids are extracted into a solvent layer, but some insoluble matters may form. Accordingly, the metallic salt is added after removing such precipitates, aggregates, and other insoluble matters from the solvent by means of, for example, centrifugal separation and/or filtration. If the insoluble matters include a small amount of phosphatidylserine, extraction operation with the alcohol can be repeated several times.

Next, the metal salt is added to the alcohol solution to thereby fractionate the phosphatidylserines extracted in the solvent layer. Specifically, most of the other phospholipids than the phosphatidylserines in the solvent layer do not precipitate by the addition of the metal salt but most of the phosphatidylserines precipitates, and thus the phosphatidylserines can be concentrated by recovering the precipitated phosphatidylserine. The metal salt can be added as a powder or a solution in a solvent such as water or an alcohol. Conditions in the procedure are not specifically limited and can be appropriately selected depending on, for example, the types and amounts of components of the mixture. More specifically, the mixture with the metallic salt is held at 10° C. to 30° C. for 30 minutes or longer to thereby insolubilize PS.

The phosphatidylserines insolubilized as a result of addition of the metallic salt can be recovered by a means such as centrifugal separation, filtration, and standing separation. The phosphatidylserines can be further purified by a conventional purification means such as column chromatography. The phosphatidylserines concentrate according to the present invention contains significantly reduced amounts of other phospholipids and other components and can thereby be relatively easily purified.

BEST MODE FOR CARRYING OUT THE INVENTION

Figure 1:
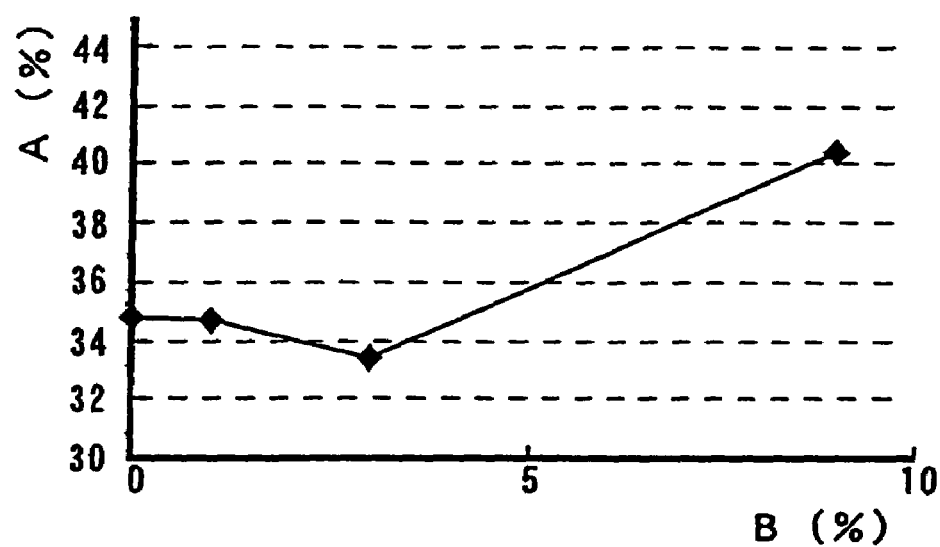
FIG. 1 is a diagram of test results on optimum amounts of MCT with the ordinate A showing the PS production rate (%) and the abscissa B showing the added amount ratio (%) of MCT to the phospholipids.

The present invention will now be explained in detail with reference to preferable embodiments below, which are not intended to limit the scope of the invention.

Example 1

Basics

A total amount of 97 g of 6.7 M L-serine aqueous solution (with or without 0.18 M calcium chloride) was kneaded (homogenized) with 100 g of a mixture of soybean lecithin and cocoa butter (NATHIN 250, trademark, available from Central Soya Company, Inc.) in an automatic mortar (Model ANM-150) and was held at 55° C. A total of amount 2.0 mL of an enzyme mixture containing 800 units of phospholipase D-Y1 derived from an actinomycete belonging to *Streptomyces* (PLD-Y1, product name, available from Yakult Honsha Co., Ltd.) was kneaded (homogenized) with the kneaded mixture in an automatic mortar, and a reaction was performed in the absence of organic solvents. The transphosphatidylation reaction was performed with stirring at 55° C. for 17 hours and was complete.

Analyses of reaction products by silica gel thin-layer chromatography revealed that 47.9% by mole of total phospholipids was converted into phosphatidylserines when 0.18 M calcium chloride was added, and that 44.5% by mole of the total phospholipids was converted into phosphatidylserines even in the absence of calcium chloride. These results show that the transphosphatidylation reaction can proceed in this reaction system even without the addition of calcium. The homogenized mixture before the initiation of the reaction was observed with a microscope under crossed Nicols and was found to have a "lamellar lyotropic liquid crystal structure substantially without phase separation".

As is described above, the present invention provides a method for performing a transphosphatidylation reaction without the use of organic solvents. Specifically, transphosphatidylated products can be efficiently produced by homogenizing an aqueous solution containing the hydroxyl-containing acceptor and phospholipase D with the phospholipid before reaction.

The method does not require any organic solvent. However, an oil-soluble substance other than organic solvents can be added to the phospholipid to thereby further improve the operability. Such oil-soluble substances include, but are not limited to, safflower oil, soybean oil, corn oil, rapeseed oil, cottonseed oil, sunflower oil, safflower oil, sesame oil, olive oil, hempseed oil, perilla oil, theobroma oil (cacao butter), coconut oil, and other vegetable oils; butter oil, fish oil, lard, beef tallow, and other animal oils; MCTs as glyceride derivatives prepared from middle-chain fatty acids as starting materials; and other edible oils and fats.

Example 2

Addition of Calcium

The results of Example 1 show that the transphosphatidylation reaction proceeds even without the addition of calcium. However, the effects of the addition of calcium were further investigated. Specifically, individual components were mixed with or without the addition of calcium as shown in Table 1 while the molar ratio of serine to the phospholipid was set at 1 or 5. The resulting mixture was kneaded (homogenized) using a microspatula and was allowed to react at 55° C. for 18 hours. In this procedure, a sample with the molar ratio of 1 employed 2.5 M serine aqueous solution, and one with the molar ratio of 5 employed 4.5 M serine aqueous solution. More specifically, NATHIN 250 and the serine aqueous solution containing, if any, calcium were mixed, and the resulting mixture was treated with the PLD-Y1 aqueous solution to initiate a reaction.

The amounts of reaction products were determined in the same manner as in Example 1. Table 2 shows that, the production rate of PS without the addition of calcium was slightly lower than but substantially the same as that with the addition of calcium. Homogenized mixtures before reaction were subjected to microscopic observation under crossed Nicols and were found to have a lamellar lyotropic liquid crystal structure substantially without phase separation. In the tables, the abbreviations PA, PE, and PI represent phosphatidic acid, phosphatidylethanolamine, and phosphatidylinositol, respectively.

TABLE 1

| | Molar ratio of serine to phospholipids | | | |
|---|---|---|---|---|
| | 1 | | 5 | |
| Addition of calcium | no | yes | no | yes |
| NATHIN 250 (g) | 10 | 10 | 10 | 10 |
| Serine (g) | 0.8 | 0.8 | 4.0 | 4.0 |
| Calcium chloride (g) | — | 0.04 | — | 0.19 |
| Water (g) | 2.6 | 2.6 | 5.7 | 5.7 |
| PLD-Y1 (units) | 82.2 | 82.2 | 82.2 | 82.2 |

TABLE 2

| | Molar ratio of serine to phospholipids | | | |
|---|---|---|---|---|
| | 1 | | 5 | |
| Addition of calcium | no | yes | no | yes |
| PA (mole %) | 13.0 | 11.8 | 10.9 | 11.0 |
| PE (mole %) | 4.7 | 3.3 | 3. | 2.7 |
| PS (mole %) | 34.5 | 35.5 | 44.2 | 47.4 |
| PC (mole %) | 31.0 | 32.2 | 25.0 | 21.4 |
| Other phospholipids (mole %) | 16.9 | 17.1 | 16.7 | 17.5 |

These results show that good yields can be obtained according to the present invention regardless of the presence or absence of calcium. Accordingly, the method of the present invention does not require the addition of calcium to its reaction system in contrast to most of conventional transphosphatidylation reactions using an organic solvent.

Example 3

Reaction with Phospholipid Containing No Triglyceride as Substrate

A total of 50 g of NATHIN 250 (available from Central Soya Company, Inc.) was dissolved in 500 mL of a reagent chemical acetone by heating to 60° C., and the solution was cooled to 15° C. The resulting precipitate was dissolved in 300 mL of a reagent chemical acetone by heating to 60° C., the solution was then cooled to 15° C. and thereby yielded a precipitate comprising phospholipids alone with no triglyceride. To 6 g of a dried product of the precipitate (hereinafter referred to "NATHIN 250/acetone precipitate") was kneaded (homogenized) with 5.8 g of 4.5M L-serine aqueous solution (with or without the addition of 0.18 M calcium chloride), and the kneaded article was held at 55° C. The kneaded article was further kneaded (homogenized) with 0.2 mL of an enzyme mixture containing 49.3 units of Phospholipase D Y-1 (available from Yakult Honsha Co., Ltd.) using a microspatula, and the kneaded article was immediately subjected to a reaction at 55° C. for 17 hours to thereby complete a transphosphatidylation reaction.

TABLE 3

PS Production Reaction Using NATHIN 250/acetone Precipitate as Substrate (Substrate Composition)

| | Molar ratio of serine to phospholipids | |
|---|---|---|
| | 5 | |
| Addition of calcium | no | yes |
| NATHIN 250/acetone precipitate (g) | 6.0 | 6.0 |
| Serine (g) | 2.4 | 2.4 |
| Calcium chloride (g) | — | 0.1 |
| Water (g) | 3.4 | 3.4 |
| PLD-Y1 (units) | 49.3 | 49.3 |

Analyses of obtained reaction products by silica gel thin-layer chromatography revealed that 41.7% of total phospholipids was converted into phosphatidylserines when 0.18 M calcium chloride was added. However, 35.1% of total phospholipids was converted into phosphatidylserines even without the addition of calcium chloride. Homogenized mixtures before the initiation of the reaction were subjected to microscopic observation under crossed Nicols and were found to have a "lamellar lyotropic liquid crystal structure substantially without phase separation". Tables 3 and 4 show compositions of substrates and the results of PS transphatidylation reactions using the acetone precipitate as a substrate, respectively.

TABLE 4

PS Production Reaction Using NATHIN 250/acetone Precipitate as Substrate (Phospholipids Compositions of Purified Products)

| | Molar ratio of serine to phospholipids 5 | |
|---|---|---|
| Addition of calcium | no | yes |
| PA (mole %) | 9.0 | 10.2 |
| PE (mole %) | 2.7 | 1.9 |
| PS (mole %) | 35.1 | 41.7 |
| PC (mole %) | 35.3 | 28.8 |
| Other phospholipids (mole %) | 17.9 | 17.4 |

Example 4

Raw material phospholipids were prepared by kneading 1 to 9% by weight of MCT (Panasate 810, trademark, available from Nippon Oil And Fats Co., Ltd.) into NATHIN 250/acetone precipitate. Each of the material phospholipids was further kneaded with 200 mg of serine and 200 mL of water (molar ratio of phospholipids to water: 0.4) relative to 500 mg of NATHIN 250/acetone precipitate. The kneaded article was further kneaded (homogenized) with a PLD-Y1 aqueous solution (4.1 units per 15 mL) using a microspatula and was allowed to react at 55° C. for 17 hours. Phosphatidylserines after the completion of reaction were determined by silica gel thin-layer chromatography.

Figure 2:
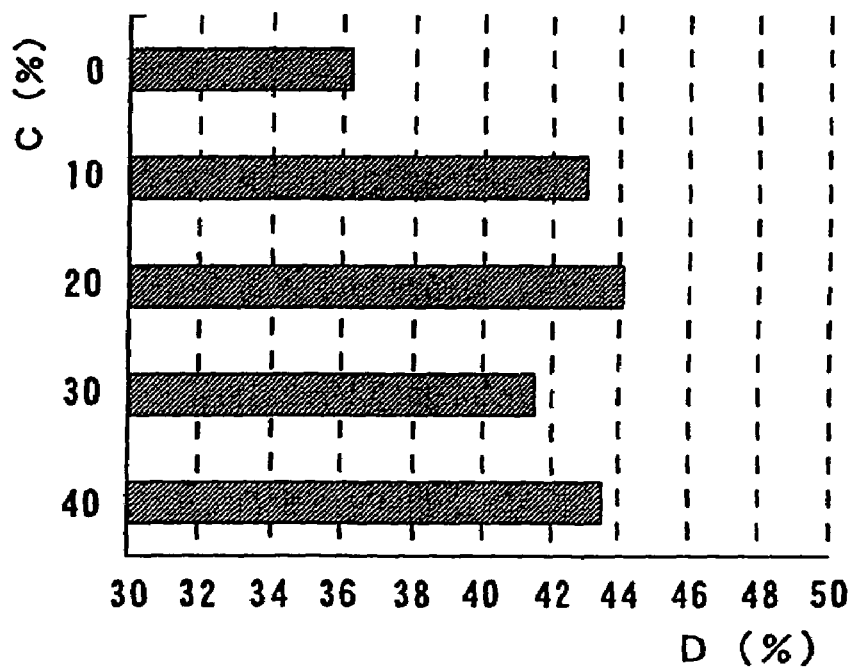
FIG. 2 is a diagram of test results on optimum amounts of MCT with the ordinate C showing the ratio (%) of MCT to the phospholipids and the abscissa D showing the PS production rate (%).

FIG. 1 is a diagram showing test results on optimum amounts of MCT. As shown in FIG. 1, by adding 50 mg (9% relative to phospholipids) of MCT, the PS production rate increases from 34.7% to 40.4% as compared with the case where MCT is not added, verifying effects of the addition of MCT. Reactions were performed in the same manner with a varying ratio of MCT of 10% to 40%. FIG. 2 is a diagram showing test results on optimum amounts of MCT. As shown in FIG. 2, the PS production rate increases in all the samples with 10% to 40% of MCT. Apparently, FIGS. 1 and 2 indicate that the amount of MCT is preferably from 9% to 40%. Homogenized mixtures before the initiation of the reaction were observed with a microscope under crossed Nicols and were found to have a "lamellar lyotropic liquid crystal structure substantially without phase separation".

Example 5

Molar Ratio of Serine to Phospholipids

To 500 mg of NATHIN 250 was added 2.5 M serine aqueous solution containing 0.18 M calcium chloride in a varying molar ratio of serine to phospholipids from 0.1 to 15, and the mixture was mixed in a mixer while warming on a water bath at 60° C. After cooling the water bath to 55° C., the reaction substrate was further mixed and homogenized with a PLD-Y1 aqueous solution using a microspatula or Vibromixer. The homogenized mixture was allowed to react at 55° C. for 17 hours, and the phospholipid composition of reaction products was analyzed by silica gel thin-layer chromatography.

Figure 3:
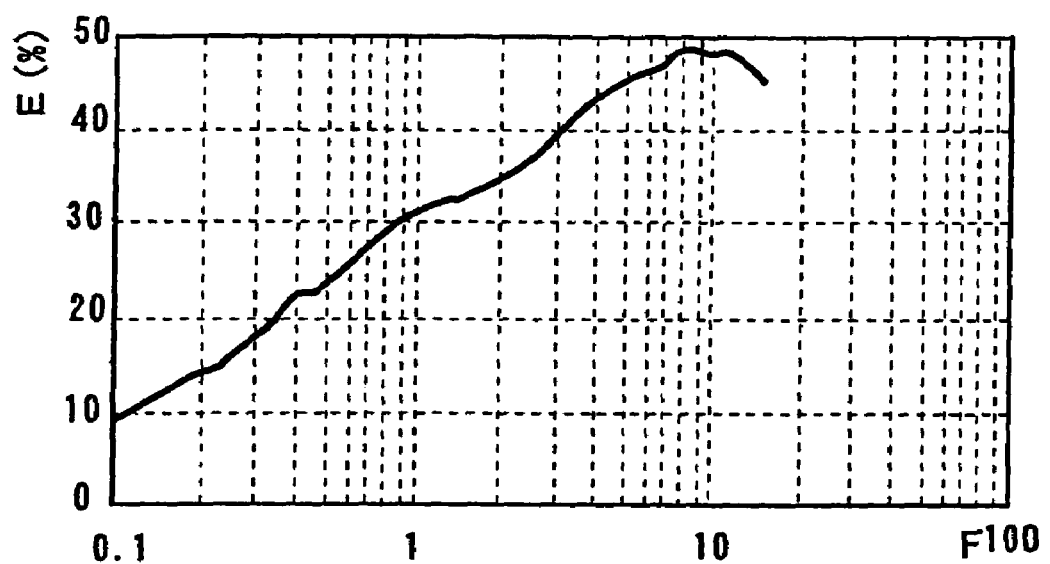
FIG. 3 is a diagram of test results on molar ratios of serine to phospholipids in a homogenized mixture with the ordinate E showing the PS production rate (%) and the abscissa F showing the molar ratio (mol/mol) of serine to the phospholipids.

FIG. 3 shows that the PS content in the reaction products is 20% or more at molar ratios of serine to phospholipids of 0.3 or more, indicating that these are suitable conditions for the production of PS. In particular, molar ratios of 4 or more can achieve PS contents of 45% or more and are typically preferred as substrate compositions. However, if the molar ratio is 10 or more, the production of PS does not increase with an increasing amount of serine, indicating that an upper limit of the molar ratio for efficient production of phosphatidylserines is about 10. Homogenized mixtures (at molar ratios from 0.3 to 10) before reaction were subjected to microscopic observation under crossed Nicols and were found to have a "lamellar lyotropic liquid crystal structure substantially without phase separation".

The amount of water relative to phospholipids was 100 parts by weight or more at molar ratios of serine of 6 or more. However, the amount of water in the homogenized mixtures as determined by the Karl Fischer's technique was 100 parts by weight or less after removal of separated water by decantation.

Example 6

Weight Ratio of Water to Phospholipids

A total amount of 200 mg each of powdery L-serine was sufficiently mixed with 500 mg of soybean lecithin (NATHIN 250/acetone precipitate, or PC 80 available from Croklaan B.V.) or egg yolk lecithin (PL-100LE, available from Q.P. Corporation) in a mortar heated at 60° C. The mixture was further kneaded with distilled water in water contents shown in FIGS. 4 to 6 and was held at 55° C. A total of 0.015 mL of an enzyme mixture containing 4.1 units of PLD-Y1 (available from Yakult Honsha Co., Ltd.) was kneaded (homogenized) with the kneaded article using a microspatula, and a transphosphatidylation reaction was performed at 55° C. for 17 hours while left stand and was complete. The water contents in the homogenized mixtures were determined by the Karl Fischer's technique.

Figure 4:
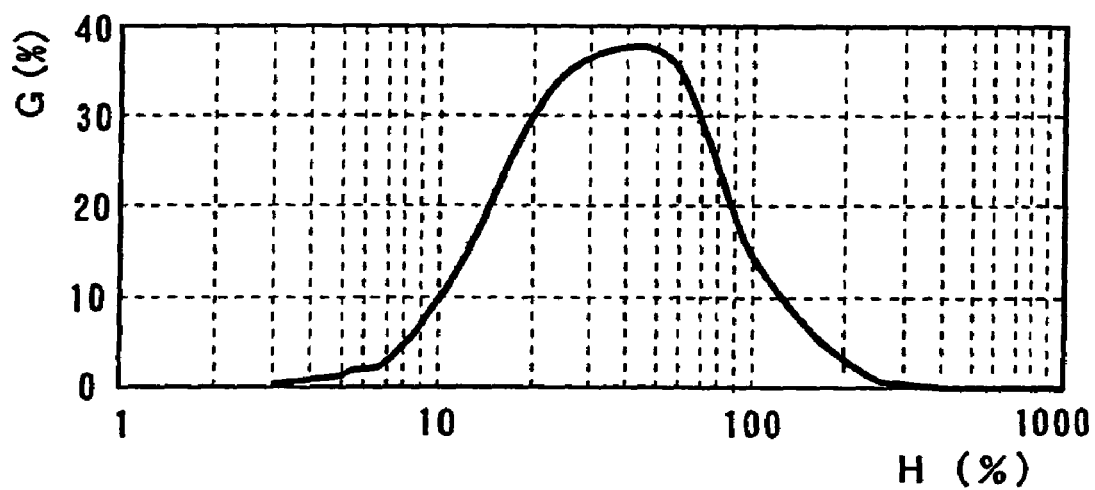
FIG. 4 is a diagram of test results on weight ratios of water to phospholipids in a homogenized mixture with the ordinate G showing the PS production rate (%) and the abscissa H showing the ratio (% by weight) of water to the phospholipids.
Figure 5:
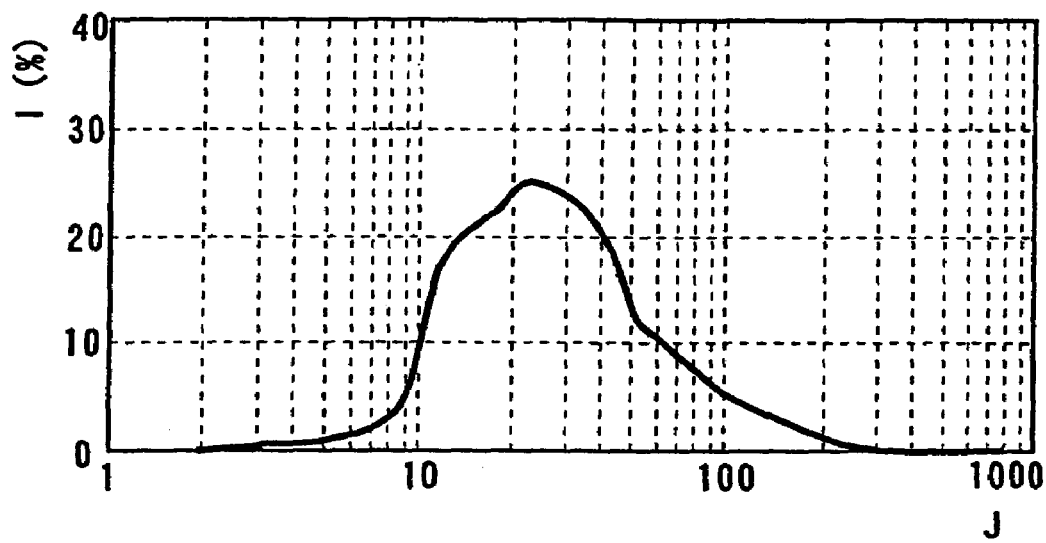
FIG. 5 is a diagram of test results on weight ratios of water to phospholipids in a homogenized mixture with the ordinate I showing the PS production rate (%) and the abscissa J showing the ratio (% by weight) of water to the phospholipids.
Figure 6:
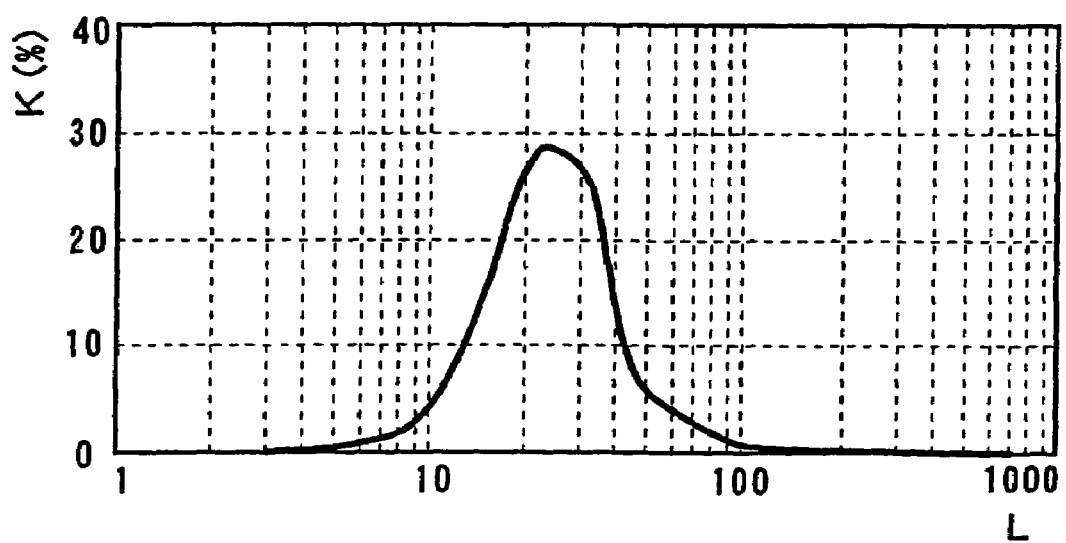
FIG. 6 is a diagram of test results on weight ratios of water to phospholipids in a homogenized mixture with the ordinate K showing the PS production rate (%) and the abscissa L showing the ratio (% by weight) of water to the phospholipids.

Obtained reaction products were analyzed by silica gel thin-layer chromatography. FIGS. 4 to 6 are diagrams of results with the ordinate showing PS contents (%) in the reaction products and the abscissa (logarithmically plotted) showing the ratio (% by weight) of water to soybean lecithin.

FIG. 4 shows that when NATHIN 250/acetone precipitate was used as a raw material phospholipid, PS was not produced at a weight ratio of water to the phospholipids in the homogenized mixture of 3%, but 10% or more of the phospholipid was converted into PS at weight ratios from 10% to 100%, indicating that these weight ratios are suitable for the production of PS. A total of 30% or more of the phospholipid was converted into PS at weight ratios of water to the phospholipids from 20% to 70%, indicating that these weight ratios are optimum for the production of PS. Homogenized mixtures were subjected to microscopic observation under crossed Nicols and were found to have a "lamellar lyotropic liquid crystal structure substantially without phase separation" at weight ratios of water to the phospholipids from 10% to 100%, suitable for the production of PS.

FIG. 5 shows that when PC 80 was used as a raw material phospholipid, PS was not produced at a weight ratio of water to the phospholipids in the homogenized mixture of 8%, but 10% or more of the phospholipid was converted into PS at weight ratios from 10% to 60%, indicating that these weight ratios are suitable for the production of PS. A total of 20% or more of the phospholipid was converted into PS at weight ratios of water to the phospholipids from 20% to 40%, indicating that these weight ratios are optimum for the production of PS. Homogenized mixtures were subjected to microscopic observation under crossed Nicols and were found to have a "lamellar lyotropic liquid crystal structure substantially without phase separation" at weight ratios of water to the phospholipids from 10% to 60%, suitable for the production of PS.

FIG. 6 shows that when the egg yolk lecithin was used as a raw material phospholipid, PS was not produced at a weight ratio of water to the phospholipids in the homogenized mixture of 8%, but 10% or more of the phospholipid was converted into PS at weight ratios from 15% to 40%, indicating that these weight ratios are suitable for the production of PS. A total of 20% or more of the phospholipid was converted into PS at weight ratios of water to the phospholipids from 20% to 35%, indicating that these weight ratios are optimum for the production of PS. Homogenized mixtures were subjected to microscopic observation under crossed Nicols and were found to have a "lamellar lyotropic liquid crystal structure substantially without phase separation" at weight ratios of water to the phospholipids from 15% to 40%, suitable for the production of PS.

Example 7

Other Than PS

Each 490 mg of aqueous solutions of acceptors indicated in Table 5 was mixed with 500 mg of PC 80 on a water bath at 60° C., the mixture was kneaded (homogenized) with 50 mL of an aqueous solution containing 13.7 units of a PLD (PLD-Y1) using a microspatula, and the kneaded article was allowed to react at 55° C. for 18 hours. Transphosphatidylation reaction products were analyzed by silica gel thin-layer chromatography.

TABLE 5

Transfer Reactions Using Acceptors other than Serine

| Acceptor as used | Concentration of aqueous solution % (w/w) | pH | Production rate of acceptor transferred lecithin (%) |
|---|---|---|---|
| Glycerol | 50 | 5.9 | 42.7 |
| L-Ascorbic acid | 41 | 5.0 | 9.4 |
| Magnesium ascorbate phosphate ester | 17 | 6.7 | 0.0 |
| Sodium ascorbate phosphate ester | 50 | 7.0 | 0.0 |
| Inositol | 17 | 6.5 | 0.0 |
| Glucose | 50 | 5.0 | 13.3 |
| Trehalose | 50 | 5.3 | 0.0 |

Table 5 shows production rates of transferred products after transfer reactions using each of the acceptors. Table 5 demonstrates that corresponding transphosphatidylated products (phosphatidylglycerol: 42.7%, phosphatidylascorbic acid: 9.4%, phosphatidylglucose: 13.3%) were produced when glycerol, L-ascorbic acid, and glucose were each used as the acceptor. In contrast, no transphosphatidylated product was produced when inositol, ascorbate phosphates, and trehalose were used.

Example 8

Reaction Temperatures

A total of 490 mg each of 4.5 M serine aqueous solution was added to 500 mg of NATHIN 250/acetone precipitate (PL) or of a phospholipid substrate (PL+TG) comprising 450 mg of NATHIN 250/acetone precipitate and 50 mg of MCT, the resulting mixture was kneaded at 60° C., was further kneaded (homogenized) with 15 mL of an aqueous solution containing 4.1 units of PLD-Y1 using a microspatula and was allowed to react at temperatures from 15° C. to 65° C. in increments of 10° C. for 18 hours. Transphosphatidylated products were analyzed by silica gel thin-layer chromatography.

Figure 7:
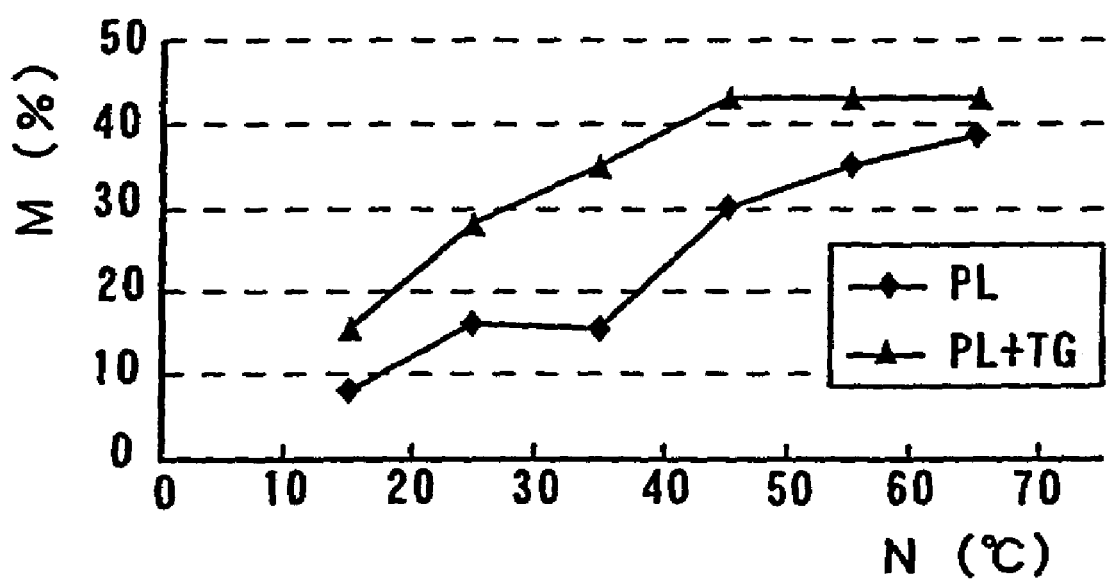
FIG. 7 is a diagram showing production rates of PS at different reaction temperatures with the ordinate M showing the PS production rate (%) and the abscissa N showing the temperature (° C.).

FIG. 7 is a diagram showing production rates of PS at different reaction temperatures and shows that the production rate of PS at 45° C. was 43% and did not change with an elevating temperature when the substrate containing NATHIN 250/acetone precipitate and MCT was used.

When the substrate containing NATHIN 250/acetone precipitate alone was used, the production rate of PS was 30.1% at 45° C. and 38.7% at 65° C., indicating that a more satisfactory result was obtained with an increasing reaction temperature. However, it is speculated that the upper limit of the reaction temperature is 65° C., since PS production decreases and the phospholipids may be deteriorated or decomposed at reaction temperatures exceeding 65° C.

Example 9

Brussels Sprout PLD

A total of 490 mg of 4.5 M serine aqueous solution (containing, if any, 9.3 mg of calcium) was mixed with 500 mg of NATHIN 250 at 55° C. After cooling to 45° C., the reaction mixture was treated with 200 mL of a liquid enzyme mixture (0.6 units per milliliter) of Brussels sprout PLD at 45° C. for 18 hours. The Brussels sprout PLD had been separately prepared according to a conventional procedure.

As a result, a reaction did hardly proceed without the addition of calcium, but proceeded and thereby yielded reaction products containing 6.2% of PS with the addition of calcium.

Example 10

Concentration of Phosphatidylserines; No. 1

With 200 g of soybean lecithin containing 40% of PC were kneaded 190 g of a serine aqueous solution containing 70 g of serine in 120 g of water and 10 mL of an aqueous solution (24 mg/mL) of phospholipase D (PLD-Y1, available from Yakult Honsha Co., Ltd.). The kneaded article was allowed to react at 55° C. for 5 hours and thereby yielded a reaction product containing 46.7% of PS in phospholipids.

A total of 5.0 g of the reaction product was extracted with 20 mL of ethyl alcohol at 45° C., and the residue (precipitate) was further extracted with two portions of 5 mL of ethyl alcohol. Three extracts were mixed, 5 mL of which was treated with 0.20 mL of 25% common salt (sodium chloride) aqueous solution, was heated to 45° C., was left stand at room temperature and thereby yielded a precipitate. As a result, the precipitate contained 62.1% of PS on dried solid matter basis, whereas a supernatant contained 3.3% of PS, indicating that PS was efficiently concentrated in the precipitated.

Example 11

Concentration of Phosphatidylserines; No. 2

A total of 50 mg of powdery sodium acetate was added to 5 mL of the mixture of the extracts obtained in Example 10, was heated to 45° C., was left stand at room temperate and thereby yielded a precipitate. As a result, the precipitate contained 61.8% of PS on dried solid matter basis, whereas a supernatant contained 3.5% of PS, indicating that PS was efficiently concentrated in the precipitate as in the use of the common salt aqueous solution.

Example 12

Concentration of Phosphatidylserines; No. 3

A 25% common salt aqueous solution was added to the mixture of the extracts obtained in Example 10 and thereby yielded insolubilized PSs. The amounts of PSs in the precipitated phospholipids and in the recovered precipitate were determined. Table 6 shows the relationship among the amount of common salt, the recovery rate of PS in the precipitate and the PS content in the phospholipids.

As shown in Table 6, PS was concentrated in a precipitated fraction under any conditions, and among them, the PS content in the precipitated phospholipids was 55% or more at amounts of common salt of 10 mmol or less per gram of the phospholipids in the extracts mixture, indicating that PS was efficiently concentrated in the precipitate. The recovery rate of PS into the precipitate was 60% or less, and 40% or more thereof remained in the supernatant at amounts of common salt of 0.05 mmol or less. These results show that PS can be concentrated into a precipitate at any amount of common salt but is practically sufficiently concentrated at amounts of common salt from 0.15 to 10 mmol per gram of phospholipids dissolved in an alcohol.

TABLE 6

Relation between Amounts of Common Salt and PS Recovery Rate/PS Contents in Phospholipids

| Common salt*[1] (mmol/g) | PS recovery rate*[2] (%) | PS content in precipitated PL*[3] (%) | PS content in supernatant PL*[4] (%) |
| --- | --- | --- | --- |
| None | — | — | 43.2 |
| 0.05 | 53.7 | 64.7 | 33.4 |
| 0.15 | 73.8 | 66.7 | 28.2 |
| 0.25 | 80.4 | 69.3 | 18.0 |
| 0.50 | 96.2 | 63.8 | 6.2 |
| 1.25 | 97.4 | 63.5 | 4.3 |
| 2.5 | 96.6 | 62.7 | 6.1 |
| 5 | 97.1 | 59.8 | 6.4 |
| 10 | 95.7 | 55.0 | 10.5 |
| 25 | 97.8 | 47.2 | 12.0 |
| 50 | 97.7 | 46.6 | 13.5 |

*[1] Ratio of amount of common salt per unit weight of phospholipids (mmol/g)
*[2] PS recovery rate into precipitated fractions (%)
*[3] PS content in precipitated phospholipids (%)
*[4] PS content in supernatant phospholipids (%)

What is claimed is:

1. A method for producing a phospholipid by transphosphatidylation comprising:
    mixing of a raw material phospholipid, a hydroxyl-containing acceptor, phospholipase D and water in the absence of an organic solvent to obtain a homogenized mixture;
    homogenizing said mixture in the absence of an organic solvent by the application of physical force to obtain a homogenized mixture in which a ratio of water to the raw material phospholipid is adjusted within the range of 10 wt % to 100 wt % so as to form a lamellar lyotropic liquid crystal structure in said homogenized mixture; and
    subjecting said homogenized mixture to a transphosphatidylation reaction at a temperature within a range from 15° to 65° C.

2. The method according to claim 1, wherein said homogenized mixture substantially has a lamellar lyotropic liquid crystal structure, without phase separation.

3. The method according to claim 1, wherein the content of said hydroxyl-containing acceptor is adjusted within a range from 0.3 mole to 10 moles per 1 mole of the raw material phospholipid in said homogenization.

4. The method according to claim 1, wherein said hydroxyl-containing acceptor is at least one hydroxyl-containing acceptor selected from the group consisting of serine, glycerol, L-ascorbic acid, glucose and choline.

5. The method according to claim 1, wherein said hydroxyl-containing acceptor is serine, which yields a phosphatidylserine.

6. The method according to claim 5, further comprising, after said transphoslphatidylation reaction:
    dissolving the phospholipid which contains said phosphatidylserine in an alcohol to obtain a solution; and
    insolubilizing the phosphatidylserine by adding a metallic salt to said solution to form an insolubilized phosphatidylserine and separating the insolubilized phosphatidylserine.

7. The method according to claim 6, wherein said metallic salt is at least one metallic salt selected from the group comprising a lithium salt, a potassium salt, and a sodium salt.

8. The method according to claim 6, wherein said metallic salt is lithium chloride, potassium chloride, or sodium chloride.

9. The method according to claim 6, wherein the alcohol is ethyl alcohol.

10. The method according to claim 1, which further comprises adding an edible oil and/or a fat during said homogenizing.

* * * * *